(12) United States Patent
Leavitt et al.

(10) Patent No.: US 6,491,634 B1
(45) Date of Patent: Dec. 10, 2002

(54) SUB-BEAMFORMING APPARATUS AND METHOD FOR A PORTABLE ULTRASOUND IMAGING SYSTEM

(75) Inventors: Steven C Leavitt, East Boothbay, ME (US); Bernard J Savord, Andover, MA (US); Benjamin M Herrick, Boxborough, MA (US); Joseph R Fallon, Boxford, MA (US); Matthew Mooney, Westford, MA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 44 days.

(21) Appl. No.: 09/687,252

(22) Filed: Oct. 13, 2000

(51) Int. Cl.⁷ ................................................ A61B 8/00
(52) U.S. Cl. ..................................................... 600/447
(58) Field of Search .................. 600/443, 447, 600/459; 310/334, 336; 367/7, 11, 138; 128/916; 73/625, 626

(56) References Cited

U.S. PATENT DOCUMENTS

| 5,229,933 A | 7/1993 | Larson, III ............. 364/413.25 |
| 5,345,426 A | 9/1994 | Lipschutz ................... 367/103 |
| 5,469,851 A | 11/1995 | Lipschutz .............. 128/661.01 |
| 5,522,391 A | 6/1996 | Beaudin et al. ........ 128/660.07 |
| 5,573,001 A | 11/1996 | Petrofsky et al. ...... 128/661.01 |
| 5,590,658 A | 1/1997 | Chiang et al. ......... 128/661.01 |
| 5,676,147 A | * 10/1997 | Petrofsky et al. ........... 600/447 |
| 5,860,924 A | 1/1999 | Quistgaard ................... 600/441 |
| 5,897,501 A | * 4/1999 | Wildes et al. ............... 600/444 |
| 5,997,479 A | 12/1999 | Savord et al. .............. 600/447 |
| 6,013,032 A | 1/2000 | Savord ........................ 600/443 |
| 6,102,863 A | 8/2000 | Pflugrath et al. ........... 600/447 |
| 6,111,816 A | * 8/2000 | Chiang et al. .............. 367/138 |
| 6,234,968 B1 | * 5/2001 | Sumanaweera et al. ..... 600/443 |

* cited by examiner

Primary Examiner—Marvin M. Lateef
Assistant Examiner—Ali M. Imam
(74) Attorney, Agent, or Firm—John Vodopia

(57) ABSTRACT

A sub-beamforming method and apparatus are applied to a portable, one-dimensional ultrasonic imaging system. The sub-beamforming circuitry may be included in the probe s assembly housing the ultrasonic transducer, thus minimizing the number of signals that are communicated between the probe assembly and the portable processor included in the imaging system. Including the sub-beamformer in the probe assembly also relieves the portable processor of some of the signal processing tasks. The sub-beamforming apparatus may be implemented digitally or may be implemented using analog components.

35 Claims, 6 Drawing Sheets

100

PORTABLE PROCESSOR

104

PROBE ASSY INCLUDING TRANSDUCER ARRAY

TARGET

108

INTERFACE CABLE

SUB-BEAMFORMING APPARATUS AND METHOD FOR A PORTABLE ULTRASOUND IMAGING SYSTEM

TECHNICAL FIELD

The present invention relates generally to ultrasound imaging systems, and, more particularly, to a sub-beamforming apparatus for use in a portable ultrasound imaging system having a one-dimensional transducer array.

BACKGROUND OF THE INVENTION

Ultrasound imaging systems have been available for quite some time and are commonly used in nondestructive testing and medical applications. Medical ultrasound imaging allows the internal structure of the human body to be viewed non-invasively in real time. Preferably, the imaging system is capable of three-dimensional imaging, thereby allowing a user the ability to easily view and diagnose complex organs, such as the heart and valves. Such an ultrasound imaging system is disclosed in commonly assigned U.S. Pat. No. 6,013,032, issued on Jan. 11, 2000 to Savord (hereafter the '032 patent), the text of which is incorporated into this document by reference. The '032 patent is directed generally to a two-dimensional ultrasound imaging method and apparatus that employs a beamforming technique that includes the formation of sub-beamformer signals. The '032 patent uses the sub-beamforming methodology on a two-dimensional transducer array to reduce the cost, size and power of the imaging system and to achieve a practical three-dimensional ultrasound imager. The '032 patent, however, only takes into account two-dimensional transducer arrays. With ever increasing pressure to reduce the size, power and cost of all medical ultrasound imaging systems, one-dimensional transducer arrays can also benefit from using sub-beamformers in the array. Two-dimensional imaging using one-dimensional transducer arrays can also benefit by requiring fewer interconnects between the probe assembly and the processor, and by reducing the size and power requirements of the imaging system.

Therefore, it would be desirable to have a portable or hand-held ultrasound imaging system that uses sub-beamforming techniques and that uses a one-dimensional transducer array.

SUMMARY OF THE INVENTION

The invention provides a portable ultrasound imaging system that uses sub-beamforming techniques and a one-dimensional transducer array.

In architecture, the present invention may be conceptualized as an ultrasound imaging apparatus including a one-dimensional ultrasonic transducer array, comprising a one-dimensional ultrasonic transducer array including a plurality of transducer elements divided into a plurality of subarrays, and receive circuitry coupled to the one-dimensional ultrasonic transducer array, the receive circuitry including a sub-beamformer configured to receive ultrasonic energy from the plurality of transducer elements and develop a plurality of delayed subarray signals corresponding to the plurality of subarrays.

The present invention may also be conceptualized as a method for sub-beamforming in a portable ultrasound imaging apparatus including a one-dimensional ultrasonic transducer array, the method comprising the steps of dividing a one-dimensional ultrasonic transducer array including a plurality of transducer elements into a plurality of subarrays, receiving, in receive circuitry coupled to the one-dimensional ultrasonic transducer array, ultrasonic energy from the plurality of transducer elements, and developing a plurality of delayed subarray signals corresponding to the plurality of subarrays.

Other systems, methods, features, and advantages of the present invention will be or will become apparent to one with skill in the art upon examination of the following drawings and detailed description. It is intended that all such additional systems, methods, features, and advantages be included within this description, be within the scope of the present invention, and be protected by the accompanying claims.

BRIEF DESCRIPTION OF THE DRAWINGS

The present invention can be better understood with reference to the following drawings. The components within the drawings are not necessarily to scale relative to each other, emphasis instead being placed upon clearly illustrating the principles of the present invention.

DETAILED DESCRIPTION OF THE PREFERRED EMBODIMENT

Although the present invention will be described below with particular reference to one-dimensional transducer arrays, the invention is applicable to any transducer array in which it is desirable to use sub-beamforming processing techniques to reduce the amount of information communicated between an ultrasonic probe assembly and the portable ultrasonic image processor.

The sub-beamforming system of the invention can be implemented in hardware, software, firmware, or a combination thereof. In the preferred embodiment(s), the sub-beamforming system is implemented using a combination of hardware and software or firmware that is stored in a memory and that is executed by a suitable instruction execution system. If implemented in hardware, as in an alternative embodiment, the sub-beamforming system can be implemented with any or a combination of the following technologies, which are all well known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA), etc.

The software portion of the sub-beamforming system, which comprises an ordered listing of executable instructions for implementing logical functions, can be embodied in any computer-readable medium for use by or in connection with an instruction execution system, apparatus, or device, such as a computer-based system, processor-containing system, or other system that can fetch the instructions from the instruction execution system, apparatus, or device and execute the instructions. In the context of this document, a "computer-readable medium" can be any means that can contain, store, communicate, propagate, or transport the program for use by or in connection with the instruction execution system, apparatus, or device. The computer readable medium can be, for example but not limited to, an electronic, magnetic, optical, electromagnetic, infrared, or semiconductor system, apparatus, device, or propagation medium. More specific examples (a nonexhaustive list) of the computer-readable medium would include the following: an electrical connection (electronic) having one or more wires, a portable computer diskette (magnetic), a random access memory (RAM) (electronic), a read-only memory (ROM) (electronic), an erasable programmable read-only memory (EPROM or Flash memory) (electronic), an optical fiber (optical), and a portable compact disc read-only memory (CDROM) (optical). Note that the computer-readable medium could even be paper or another suitable medium upon which the program is printed, as the program can be electronically captured, via for instance optical scanning of the paper or other medium, then compiled, interpreted or otherwise processed in a suitable manner if necessary, and then stored in a computer memory.

Figure 1:
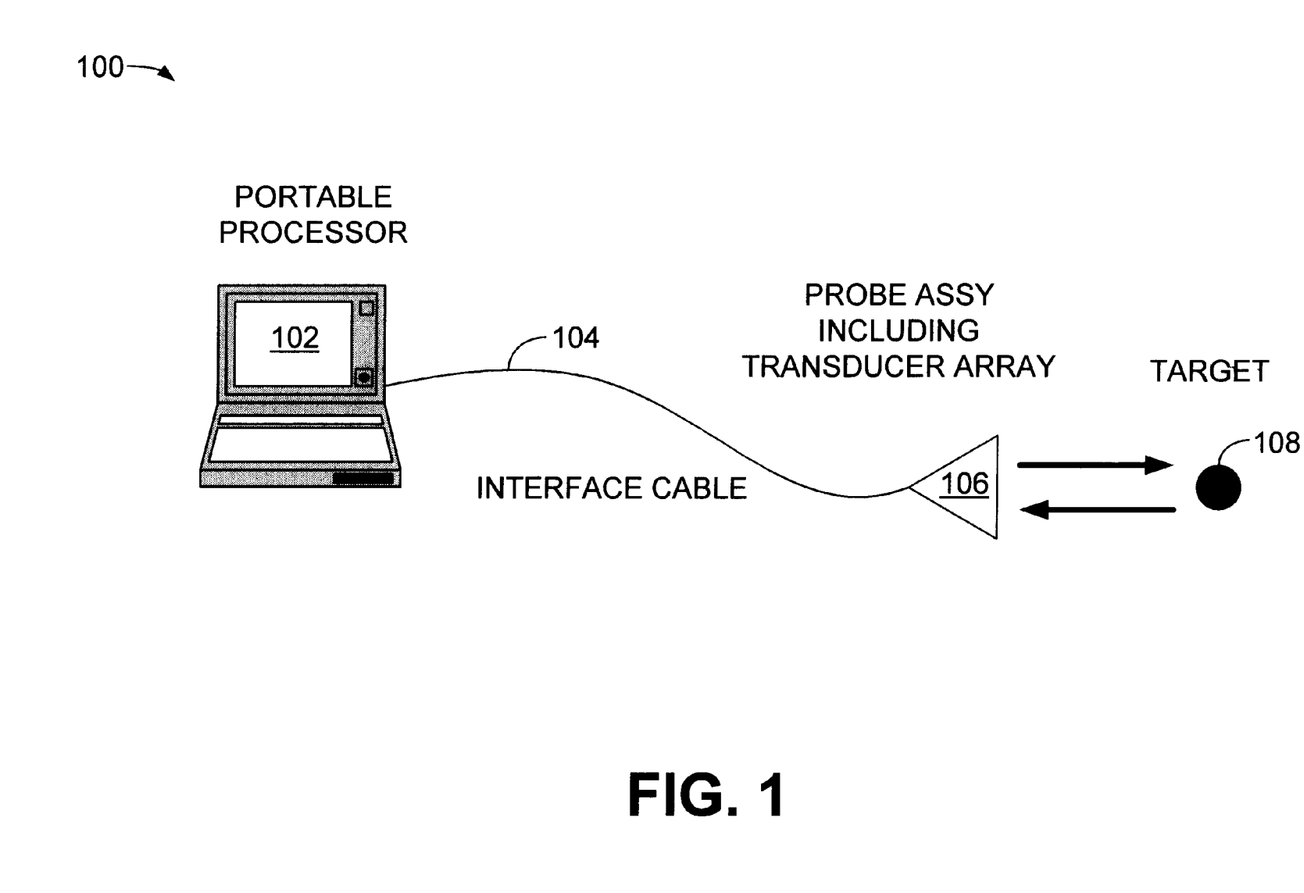
FIG. 1 is a graphical view illustrating a portable ultrasound system constructed in accordance with an aspect of the invention.

Turning now to the drawings, FIG. 1 is a graphical view illustrating a portable ultrasound system 100 constructed in accordance with an aspect of the invention. Portable ultrasound system 100 includes portable processor 102 connected via interface cable 104 to probe assembly 106. Probe assembly 106 transmits ultrasonic energy to target 108 and receives reflected ultrasonic energy from target 108. The ultrasonic energy reflected from target 108 is received by a transducer array included within probe assembly 106. The received ultrasonic energy is processed in the probe assembly and forwarded to the portable processor for additional processing. After processing, an image generated from the received ultrasonic energy is then displayed on a display incorporated within portable processor 102. In accordance with an aspect of the invention, probe assembly 106 includes processing circuitry that enables some of the ultrasound energy received from target 108 to be processed into a number of sub-beams. These sub-beams represent the energy received from all of the transducers in probe assembly 106 using a number of signals less than that of the number of transducer elements. This in turn reduces the number of signals that must be communicated between probe assembly 106 and portable processor 102 via interface cable 104. Probe assembly 106 includes sub-beamformer circuitry (to be described below with respect to FIG. 2) implemented using digital electronics, that form a number of delayed sub-array signals using multiple partial beamforming techniques. The probe assembly 106 also contains transmit application specific integrated circuit(s) ASIC(s) (to be described with respect to FIG. 2), which provide the transmit high voltage pulses to the transducer array (not shown) contained within probe assembly 106.

Figure 2:
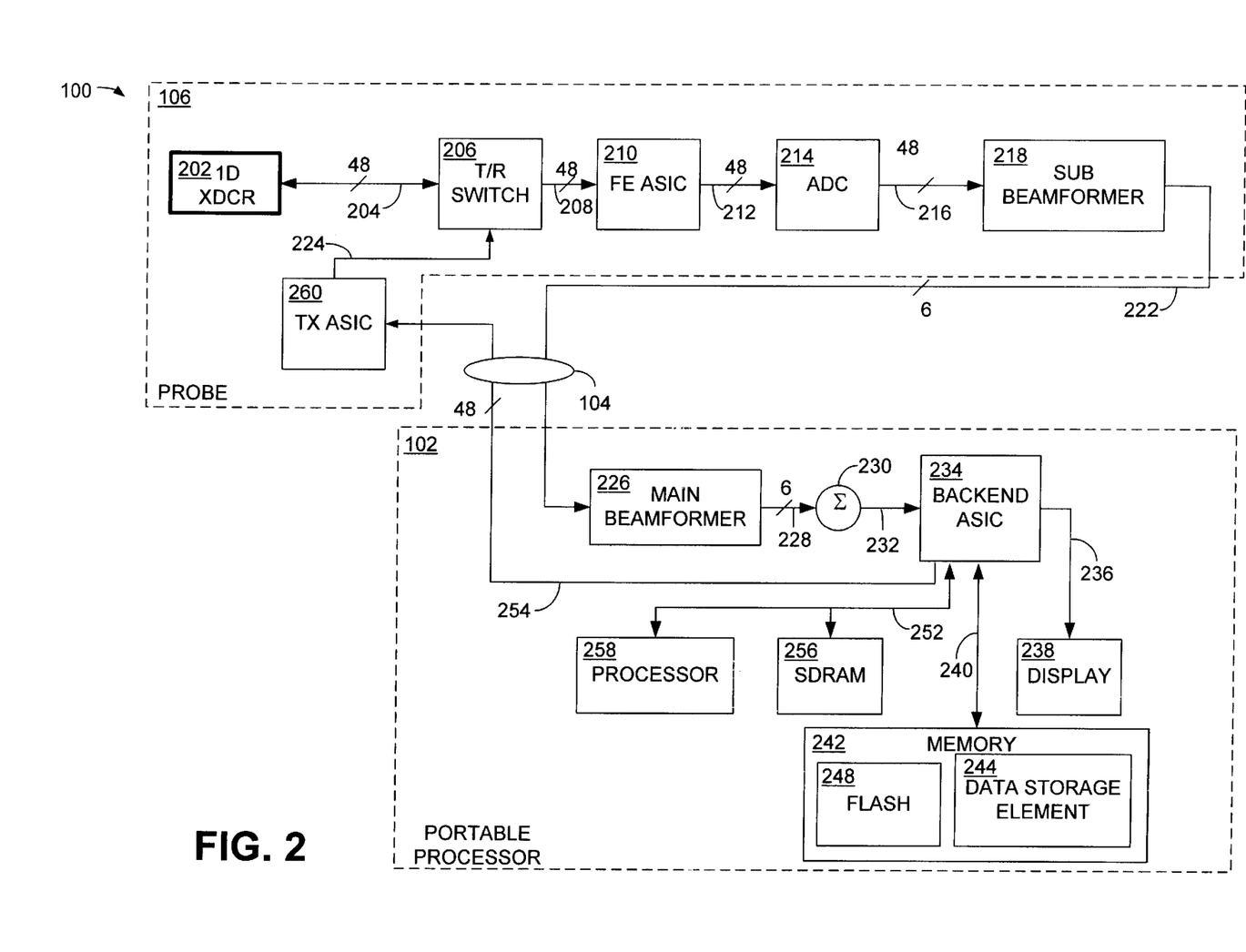
FIG. 2 is a schematic view illustrating the portable ultrasound system of FIG. 1.

FIG. 2 is a schematic view illustrating the portable ultrasound system 100 of FIG. 1. Probe assembly 106 includes one-dimensional transducer array 202. One-dimensional transducer array 202 includes a number of individual ultrasonic transducer elements arranged as a phased array, linear array, or curved linear array. It is contemplated that any one-dimensional transducer array can be used in the disclosed system, however, for discussion purposes, a 48-element phased array transducer will be described. Transducer array 202 communicates 48 signals (one signal for each transducer element) via connection 204 with transmit/receive (T/R) switch 206. T/R switch 206 provides the switching function that isolates the transmit energy from the receive energy. T/R switch 206 communicates via connection 208 with a plurality of processors, commonly referred to as "front-end" ASICs, an exemplar one of which is illustrated as front-end ASIC 210. Front-end ASIC 210 is typically an analog ASIC device, and receives a portion of the 48 ultrasonic transducer signals via connection 208. While illustrated using a single front-end ASIC 210, a plurality of front-end ASICs are typically employed to process all of the 48 ultrasonic transducer signals received via connection 208. Front-end ASIC 210 performs power amplification, filtering and front-end time gain compensation (TGC) functions. TGC is required when receiving ultrasound signals from multiple depths within the target. In such an instance, in order to compensate for the increasing time of flight with respect to depth of the ultrasonic energy, gain is typically increased correspondingly. Front-end ASIC 210 supplies the amplified, filtered and gain compensated ultrasonic energy signals via connection 212 to a plurality of analog-to-digital converters (ADCs), an exemplar one of which is illustrated using reference numeral 214. The plurality of ADCs 214 convert the 48 analog signals on connection 212 into a digital bit stream using 8-bit converter technology, and supply the digital bit stream to a plurality of sub-beamformers, an exemplar one of which is illustrated using reference numeral 218, via connection 216. Although shown as single blocks, front-end ASIC 210, ADC 214 and sub-beamformer 218 are typically implemented in multiples sufficient to process the signals received from the transducer elements contained within transducer 202. Furthermore, the ADC 214 and the sub-beamformer 218 may be combined and implemented in one or more ASICs.

A portion of the 48 ultrasonic signals represented by the digital bit stream on connection 216 are forwarded to each sub-beamformer 218. Each sub-beamformer 218 provides partial beamforming by combining a portion of the 48 input signals on connection 216 into a smaller number of delayed sub-array signals. The plurality of sub-beamformers process all of the 48 ultrasonic signals on connection 216 to provide the delayed subarray signals on connection 222. Sub-beamformer 218 can be implemented as disclosed in commonly assigned U.S. Pat. No. 6,013,032 referenced above, or can be implemented using an all digital circuitry to be described below. Whether implemented as disclosed in the above-referenced U.S. Pat. No. 6,013,032 or whether implemented using an all digital approach, sub-beamformer 218 provides multiple partial beamforming within probe assembly 106. In this manner, the amount of processing required to be performed by portable processor 102 and the number of signals that are communicated via interface cable 104 can be significantly reduced. The operation of sub-beamformer 218 will be described in further detail below with respect to FIGS. 3, 4, 5 and 6.

The output of the plurality of sub-beamformers 218 is a plurality of delayed sub-array signals and is supplied via connection 222 to main beamformer 226. For illustrative purposes only, the 48 individual transducer signals present on connection 216 are formed into six delayed sub-array signals by sub-beamformer 218 and supplied via connection 222. These six delayed sub-array signals are supplied to main beamformer 226, which can be implemented in similar fashion as sub-beamformer 218. Main beamformer 226 can be implemented in ASICs or can be implemented in a discrete block as described in FIG. 2, or can be combined into one ASIC with ASIC 234, commonly referred to as "back-end" ASIC 234. The outputs of main beamformer 226 on connection 228 are combined in summing device 230 so that a single beamformed output signal is present on connection 232. The single beamformed output signal on connection 232 is supplied to back-end ASIC 234. Back-end ASIC 234 provides detection and additional back-end TGC functionality. Detection includes converting the radio frequency (RF) data stream produced on connection 232 into log magnitude data sampled for two-dimensional anatomical imaging as well as baseband quadrature data for use in two dimensional color flow imaging.

Back-end ASIC 234, which may be implemented using a plurality of ASICs, communicates via connection 252 with processor 258 and with static/dynamic random access memory (SDRAM) 256. Processor 258 controls the operation and functionality of the portable ultrasound system 100 by executing the code contained in SDRAM 256 and flash memory 248, and, for illustrative purposes only, can be a series 7xx power PC processor available from Motorola Corporation. Back-end ASIC 234 also communicates with memory element 242 via connection 240. Memory element 242 includes flash memory 248 and data storage element 244. Data storage element 244 can be used to initially load the flash memory 248 and can also be used to export information displayed on display 238. Although shown using discrete connections, processor 258, SDRAM 256 and memory 242 may also communicate over a common bus.

Back-end ASIC 234 also provides a scan converter function in order to provide an ultrasound image for display via connection 236 on display element 238. For example, display element 238 can be a liquid crystal display (LCD) used to view the ultrasound images generated by the probe assembly 106 and the portable processor 102. Although omitted for clarity, portable processor 102 also includes a power source, such as a battery or AC adapter for powering all the elements disclosed in FIG. 2. Back-end ASIC 234 also communicates with transmit ASIC 260 via connection 254. Similar to that of the other ASICs described herein, transmit ASIC 260 is typically implemented as a plurality of ASICs, but will be described using transmit ASIC 260 for simplicity. Transmit ASIC 260 develops the transmit pulses that are used to excite the elements in transducer array 202, and are communicated to T/R switch 206 via connection 224. The combination of connections 222 and 254 form interface cable 104 of FIG. 1. In some applications, the functionality of TX ASIC 260 could be incorporated into the front-end ASIC 210 and in other applications, the functionality of the TX ASIC could be incorporated into the portable processor 102.

Figure 3:
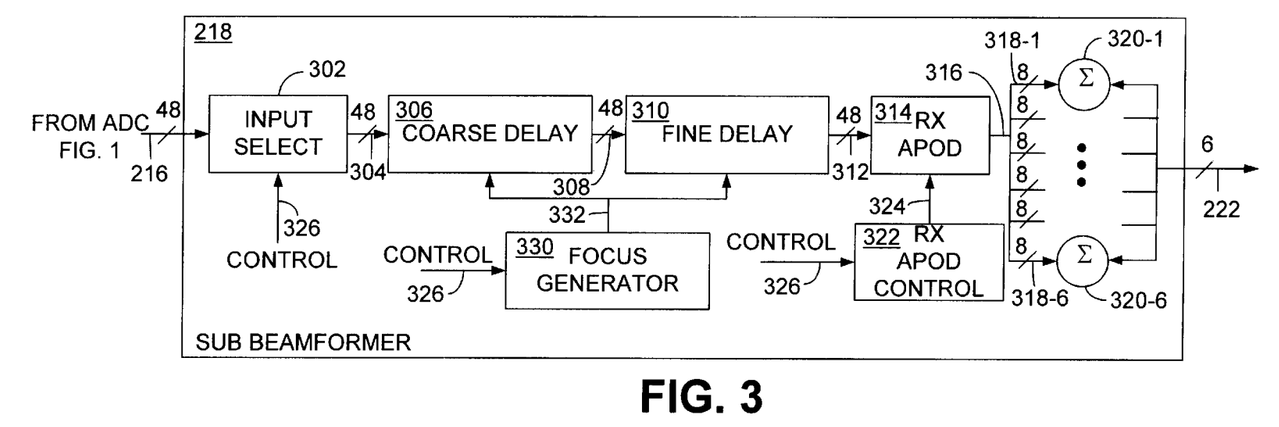
FIG. 3 is a schematic view illustrating the sub-beamformer of FIG. 2.

FIG. 3 is a schematic view illustrating the sub-beamformer 218 of FIG. 2. Sub-beamformer 218 receives the digital bit stream from ADC 214 on connection 216. Input select element 302 receives a control signal via connection 326 from a beamformer configuration register (not shown) that determines whether the input mode will be set to test or normal. The input select element 302 allows for inputting a digital test vector into each of the channels for exercising the beamformer. The output is checked for the correct vector. In normal imaging mode, the input select element 302 passes the 48 ADC outputs to the corresponding 48 coarse delay input channels. The output of input select element 302 is supplied via connection 304 to coarse delay element 306. Coarse delay element 306 employs a synchronous dual port RAM device (to be described below with respect to FIG. 4) to provide a coarse delay to each of the signals on connection 304, and provides this delayed signal via connection 308 to fine delay element 310. The control of coarse delay element 306 and fine delay element 310 will be described in further detail below with respect to FIG. 5.

Fine delay element 310 provides further filtering to the signal on connection 308 and supplies the filtered signal on connection 312. The operation of fine delay element 310 will be described in further detail below with respect to FIG. 6. Focus generator 330 provides the coarse and fine delay control values via connection 332 to coarse delay element 306 and fine delay element 310, respectively. The focus generator 330 receives a control signal via connection 326 in the form of a gate signal that starts the data transfer process. The gate signal is generated by the back-end ASIC 234 with the aid of internal line counters (timers). The line counters are started under command of the processor 258.

The output of fine delay element 310 on connection 312 is supplied to receive (RX) apodization (APOD) element 314. The RX APOD element 314 multiples the samples on connection 312 by a value between 0 and 1 and will be described in further detail with respect to FIG. 7. RX APOD element 314 is controlled by RX APOD control element 322, which receives a control signal via connection 326. The control 326 is generated by the back-end ASIC 234 along with control from the processor 258. The output of RX APOD element 314 on connection 316 is illustrated as six signals, each going to a summing element 320-1 through 320-6. Each of the six signals on connection 316 is represented by 8 individual signals, each one a 12-bit signal on connections 318-1 through 318-6. Each of the summing elements 320-1 through 320-6 provides a single delayed sub-array signal comprising 14 bits, resulting in six delayed sub-array signals supplied via connection 222 to the main beamformer 226 (FIG. 2).

Figure 4:
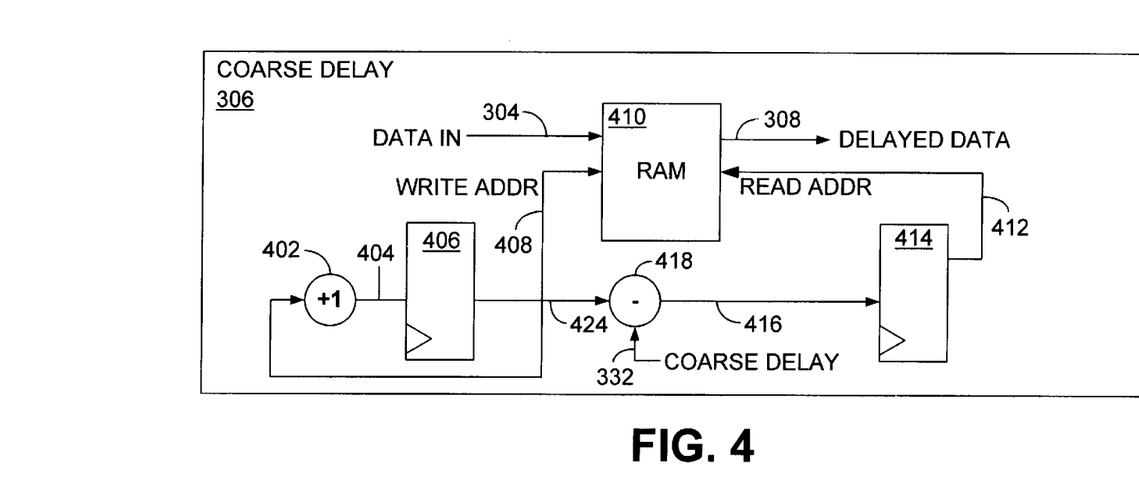
FIG. 4 is a schematic view illustrating the coarse delay element of FIG. 3.

FIG. 4 is a schematic view illustrating the coarse delay element 306 of FIG. 3. Data samples from the input select element 302 of FIG. 3 are supplied via connection 304 to a random access memory (RAM 410. RAM 410 is preferably a synchronous dual port RAM device. The data samples are stored in the RAM 410 sequentially for each sample clock. The input write address on connection 408 increments by one for every sample. The address rolls over when it reaches the end of the RAM 410. The delayed RAM output read address on connection 412 points to a location, which is a variable number of samples behind the input address. The read address signal on connection 412 is supplied by register 414 and the write address signal on connection 408 is supplied by register 406 after being incremented by one cycle by increment element 402. This offset establishes the coarse delay, which is defined by the focus generator 330 (to be described below with respect to FIG. 5). The output address on connection 412 always lags the input address on connection 408 by the amount of the coarse delay +1. The "+1" term is added to the offset to prevent simultaneous access to the same read and write address.

As the amount of coarse delay remains constant in the RAM 410, both the input and output address pointers (write address 408 and read address 412, respectively) increment by one for each sample clock, offset in value by delay +1. However, when the amount of coarse delay is incremented by the focus generator 330 (FIG. 5), the RAM 410 is "stalled" by one sample. This occurs because the output address pointer on connection 412 does not change. The RAM 410 then outputs the same sample that was output during the previous sample clock cycle before the delay was incremented. This allows the pipeline to be incremented in length to route the RAM 410 without disrupting the sequence of data for the next stage in the beamformer. The output of RAM 410 on connection 308 is the coarse delayed data that is then supplied to fine delay element 310. The coarse delay signal on connection 332 is supplied by the focus generator 330 to the delay element 418. The delay element 418 subtracts an integer number from the signal on connection 424.

The signal supplied via connection 332 is of the form "x.y" where "x" is an integer number that is used as the coarse delay value. The integer number specifies the number of integer addresses that the read address will trail the write address. The "y" portion specifies the fine delay value and is a two-bit number quantifying the fine delay to be ¼, ½, ¾ or 1 corresponding to the digital codes 01, 10, 11 and 00. The +1 in the write path 402 is used to lag the read address from the write address by the value one. The +1 in element 402 is the minimum offset value. A simple example clarifies the use of the coarse and fine delays. Assume the current delay expressed as a "x.y" number is 4.75 and should increment by ¼ for each successive clock cycle in order to have the correct delays. The coarse delay would be set for 4 and the fine delay would be set for ¾. On the next clock cycle, the coarse delay would stay at 4 and the fine delay would advance to 1, providing the desired 5 clock cycle delay. With the next clock, the coarse delay would advance to 5 and the fine delay would advance to ¼ providing the required 5.25 clock cycle delay.

Figure 5:
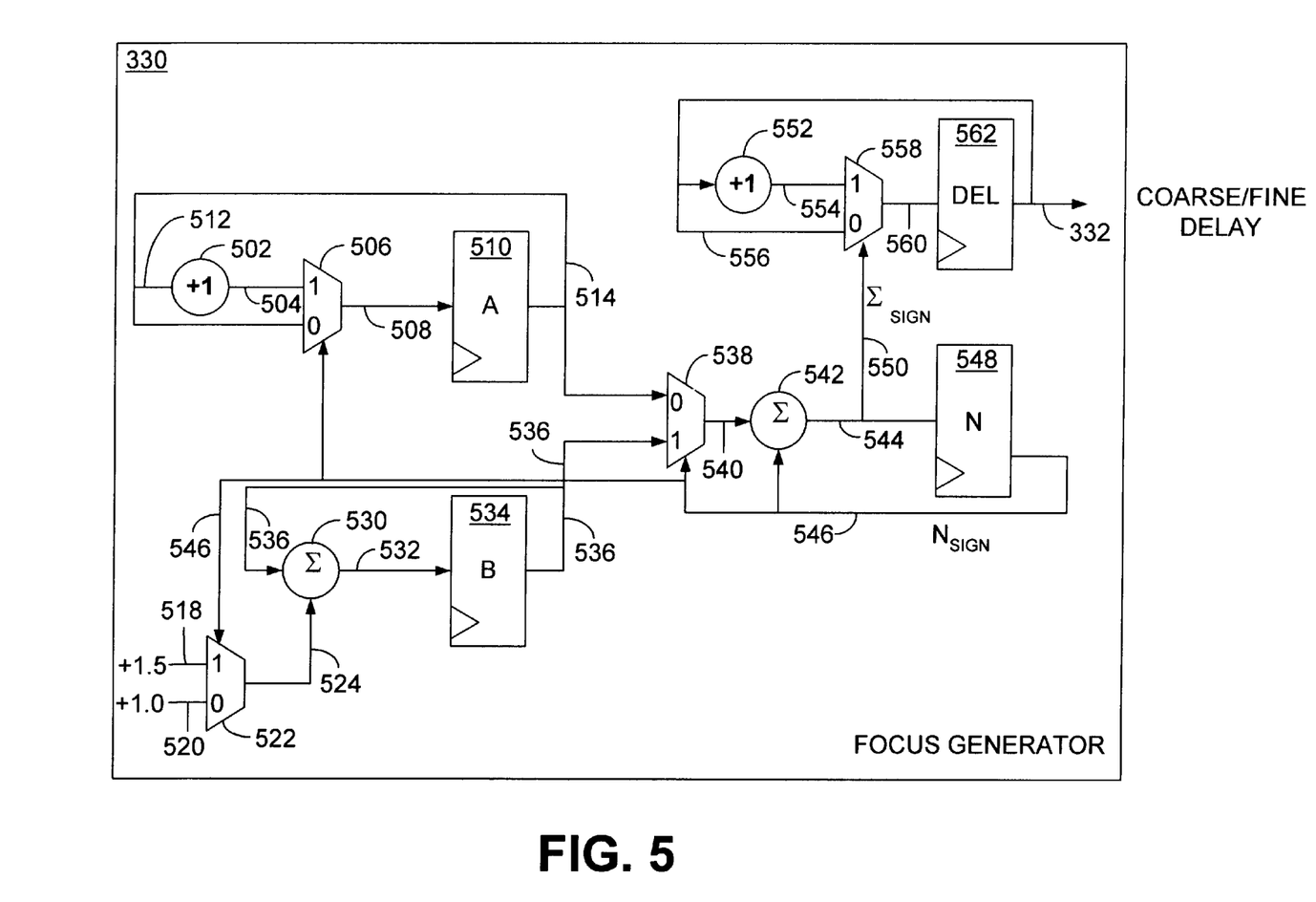
FIG. 5 is a schematic view illustrating the focus generator of FIG. 3.

FIG. 5 is a schematic view illustrating the focus generator 330 of FIG. 3. Focus generator 330 produces both the coarse and fine delay values that are supplied to the coarse delay element 306 and the fine delay element 310, respectively. As a scan line is received by the sub-beamformer 218, these delay values are incremented by amounts based on the "focusing equation," which geometrically considers the difference in distances between the elements in the transducer array 202 of FIG. 1 from the desired image location in the scan plane. The wave front produced by the returning received ultrasonic energy is delayed independently by each channel so that when the delayed values are summed together the result is the image intensity for that point in the scan plane.

The focus generator 330 is started after a programmable focus-hold time, which is used to prevent imaging in areas that cannot be focused because of their distance and angle with respect to the transducer face. The focus gate signal is generated by counting down a programmable counter (not shown) to zero after the virtual start of beamforming (VSB) has occurred. The focus gate signal delays the focusing for a channel until that channel can contribute to beam formation. Thus, center elements in the transducer array are the first to contribute to the beamformed sum and as such have a short focus gate signal. Conversely, whereas the outer elements of the transducer array have longer focus gate delays in order to hold off their contribution to the beamformed sum until the beamformer applies appropriate delay for the particular channel. The VSB signal is a universal hold-off initiated after the start of transmit and is used for all channels until the data at the output of the ADC's (214 of FIG. 2) is valid. When the data is valid the focus gate signals start their hold-offs for each individual channel. These signals are part of the control signals 326 (FIG. 3) that operate the focus generator 330.

The focused gate signal is sent to the channels' delay RAM section (410 of FIG. 4) to control the flow of data at its RAM output 308 (FIG. 4). The focus generator 330 includes registers 510, 534 and 548, each of which is seeded at the start of a scan line with values defined by the transducers' operating parameters (frequency, pitch, element number, scan angle). Once the focus-hold period elapses, the three registers will operate as follows. Register 510 increments by one every sample clock if the output of register 548 on connection 546 is negative. If the output of register 548 on connection 546 is positive, the value of register of 510 will not change. The input to register 510 is supplied via connection 508 from multiplexer 506, which receives an input either from the output of register 510 on connection 514 or from +1 element 502 via connection 504.

The register 534 increments by a value of 1.5 if the output of register 548 on connection 546 is negative. If the output of register 548 on connection 546 is positive, then the register 534 will increment by a value of 1 on every sample clock. The input to register 534 is supplied via connection 532 from summing element 530. Summing element 530 receives the output of multiplexer 522 via connection 524 and the output of register 534 via connection 536.

The register 548 increments by the value of the register 534 if the output of register of 548 on connection 546 is negative. If the output of register 548 on connection 546 is positive the value of register 548 increments by the value of the output of register 510 on connection 514. The input to register 548 on connection 544 is supplied by the summing element 542, which receives the output of register 548 on connection 546 and also receives the output of multiplexer 538 via connection 540.

The operation of registers 510, 534 and 548 results in one bit (specifically the most significant bit "MSB" of the value that is added to the register 548 during its increment cycle) on connection 544 and labeled $\Sigma_{SIGN}$. This signal input on connection 550 instructs the multiplexer 558 to supply either a one or a zero on connection 560 to fractional delay register 562. The output of fractional delay register 562 provides the coarse and fine delay signals via connection 332. If the value of the signal on connection 550 is logic 1 (meaning that the output of register 548 is negative) the fractional delay register 562 increments. The output of fractional delay register 562 is used to select the fine delay value in the fine delay all-pass filter stage (to be described below with respect to FIG. 6). The output of fractional delay register 562 can be considered a fractional delay because it defines the fractional portion of a sample clock over which the samples are delayed. If this fine delay value, which is 2-bits in length, is zero when incremented, then the coarse delay value is also incremented by one. The coarse delay value defines the offset of the read and write address pointers (connections 412 and 408, respectively, of FIG. 4) for the RAM 410. This delay is also referred to as the integer delay since it represents the delay in full sample clocks.

The focus generator also generates a "stall" signal that is active when the coarse delay increments. The stall signal, which is included in the coarse delay signal on connection 332 (FIG. 4), is used to hold the data in the all-pass filter taps (FIG. 6) for one sample clock. This is so because the data from the RAM 410 (FIG. 4) is stalled by one sample as the read/write offset increments. Both the stall signal and the fractional delay bits are pipelined to align themselves with the appropriate data samples in the all-pass filter (FIG. 6).

Figure 6:
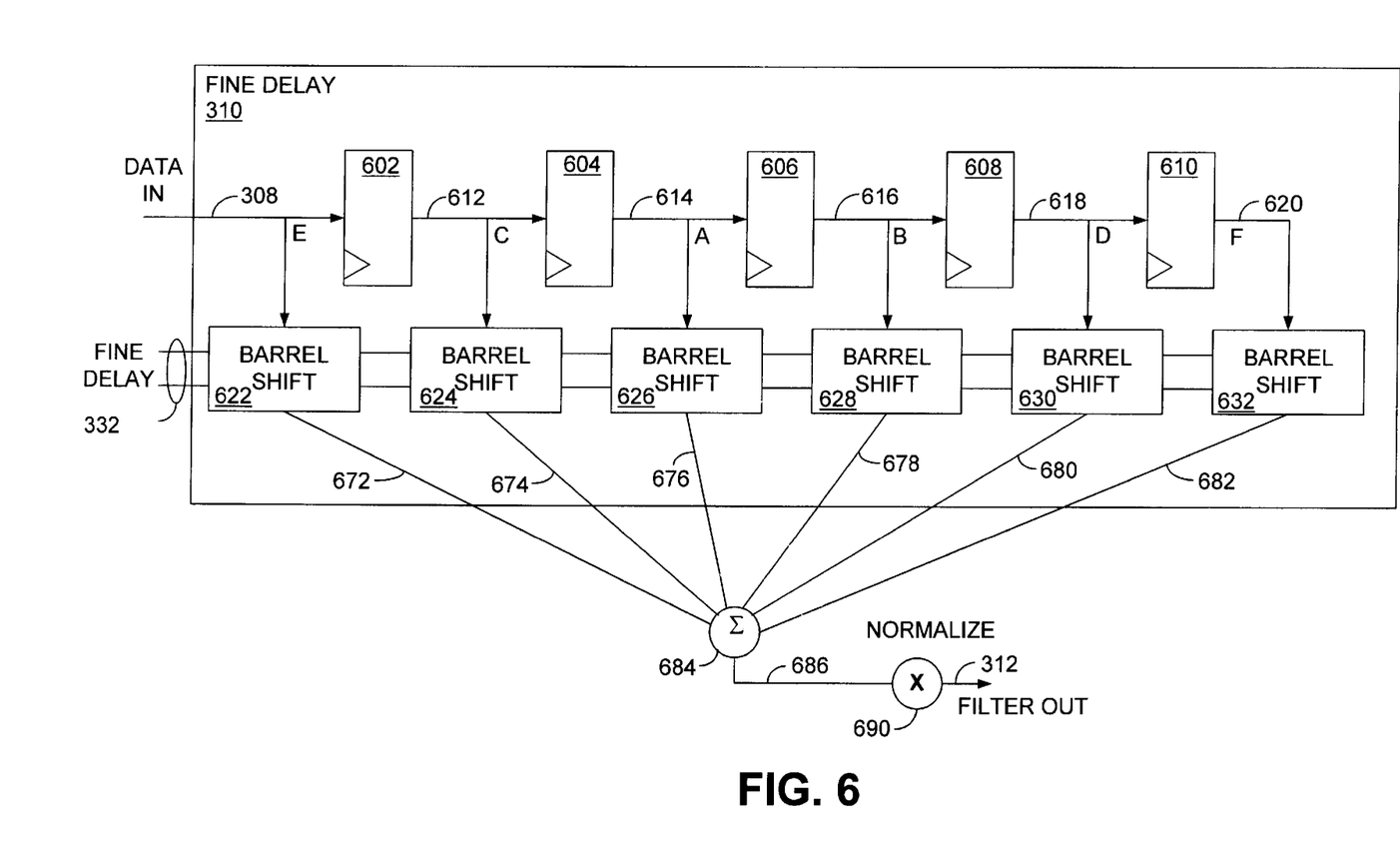
FIG. 6 is a schematic view illustrating the fine delay element of FIG. 3.

FIG. 6 is a schematic view illustrating the fine delay element 310 of FIG. 3. The "coarse delayed samples" on connection 308 are clocked into the fine delay element 310. The fine delay element 310 includes a plurality of registers 602 through 610 and a corresponding plurality of barrel shifters 622 through 632. The focus generator 330 (FIG. 5)

determines the amount by which to delay the sample data for the fine delay element 310, and sends a fractional delay value to the fine delay element 310 via signal lines 332. The signal on connection 332 from the focus generator 330 selects one of four filters to be applied to incoming samples on connection 308. The four filters are designed to delay the samples by ¼, ½, ¾, or 1 sample. The 1 sample delay filter has an inherent pipeline delay of three so that the fractional delays are 2.25, 2.50, 2.75 and 3 samples, respectively. The fine delay element 310 includes 6 taps where each tap includes one of the registers 602, 604, 606, 608 and 610 wherein the output of the RAM 410 of FIG. 4 is actually the first tap register noted as tap "E" on connection 308. These taps can be thought of as stages of delay and are fed to the barrel shifters 622, 624, 626, 628, 630 and 632 via connections 308, 612, 614, 616, 618 and 620, respectively. The tap registers 602, 604, 606, 608 and 610 form a shift register and the input to the fine delay element 310 is clocked into the first register 602. This shift register is "stalled" when the coarse delay pipeline is incremented because the delay RAM 410 of FIG. 4 is essentially stalled when the read/write pointer offset is incremented. This means that the filter taps are not shifted to the next sample during a stall. Instead, they operate on the same samples as those that occurred before the stall.

Each filter contains coefficients whose values are (1/power of 2). This allows the taps to be implemented with the simple barrel shifters 622, 624, 626, 628, 630 and 632 instead of using more complicated multipliers. Depending upon the desired filter pass characteristic, a barrel shifter is selected by the fine delay value supplied from focus generator 330 on connection 332.

The data on connection 308 is supplied both to register 602 and barrel shifter 622. After the data on tap "E" 308 has been barrel shifted according to the coefficient for tap "E" shown in following Table 1, the output of barrel shifter 622 is supplied via connection 672 to summing element 684. Similarly, the output of register 602 is supplied on connection 612 both to register 604 and to barrel shifter 624. The barrel shifter 624 connected to tap "C" barrel shifts the data (multiplies) again according to the following Table 1 with the output of barrel shifter 624 to be supplied on connections 674 to summing element 684. The fine delay input on connection 332 is also supplied to barrel shifter 624. Similarly, the fine delay signal on connection 332 is supplied to barrel shifters 626, 628, 630 and 632. The output of register 604 on connection 614 is also supplied to barrel shifter 626, which uses the filter coefficient corresponding to tap "A". The output of barrel shifter 626 is supplied via connection 676 to summing element 684. Similarly, the output of register 606 is supplied on connection 616 (including a coefficient weight corresponding to tap "B") is supplied to barrel shifter 628 the output of which is supplied on connection 678 to summing element 684. In a similar manner, the outputs of barrel shifters 630 and 632 are also supplied on connections 680 and 682, respectively, to summing element 684. The output of summing element 684 on connection 686 is multiplied by a normalization factor in multiplier 690. The normalization factor depends upon the particular fine delay filter that is being applied to the sample data. The filter coefficients on taps A through E and the normalization factor 690 are shown in Table 1 below for each of the filters.

TABLE 1

|  | COEF 1 (E) | COEF 2 (C) | COEF 3 (A) | COEF 4 (B) | COEF 5 (D) | COEF 6 (F) | NORMALIZE FACTOR |
|---|---|---|---|---|---|---|---|
| DELAY = ¼ | ¹⁄₁₆ | −¼ | ½ | ½ | −⅛ | ¹⁄₁₆ | 0.75 |
| DELAY = ½ | ¹⁄₁₆ | −¼ | 1 | 1 | −¼ | ¹⁄₁₆ | 0.75 |
| DELAY = ¾ | ¹⁄₁₆ | −⅛ | ½ | ½ | −¼ | ¹⁄₁₆ | 0.75 |
| DELAY = 1 | 0 | 0 | 0 | 2 | 0 | 0 | 0.625 |

The normalization factors are determined based on the average gain of the filters over a bandwidth around the RF (radio frequency), which is typically the sample frequency divided by four. Also, in order to maximize dynamic range in the output of the filter, the gains are selected so that the output comes as close as possible to full scale without overflowing (or wrapping) for any possible data set. The worst case data set is 8-bit full scale values whose signs follow the signs of the filter taps. The output of multiplier 690 on connection 312 is then supplied to the RX APOD element 314 (see FIG. 3).

It should be noted that the operation of the front-end ASIC 210, analog-to-digital converter 214, sub-beamformer 218, main beamformer 226, back-end ASIC 234 and the portable processor 102 may be controlled using software code stored in SDRAM 256 and flash memory 248 and executed in processor 258.

Figure 7:
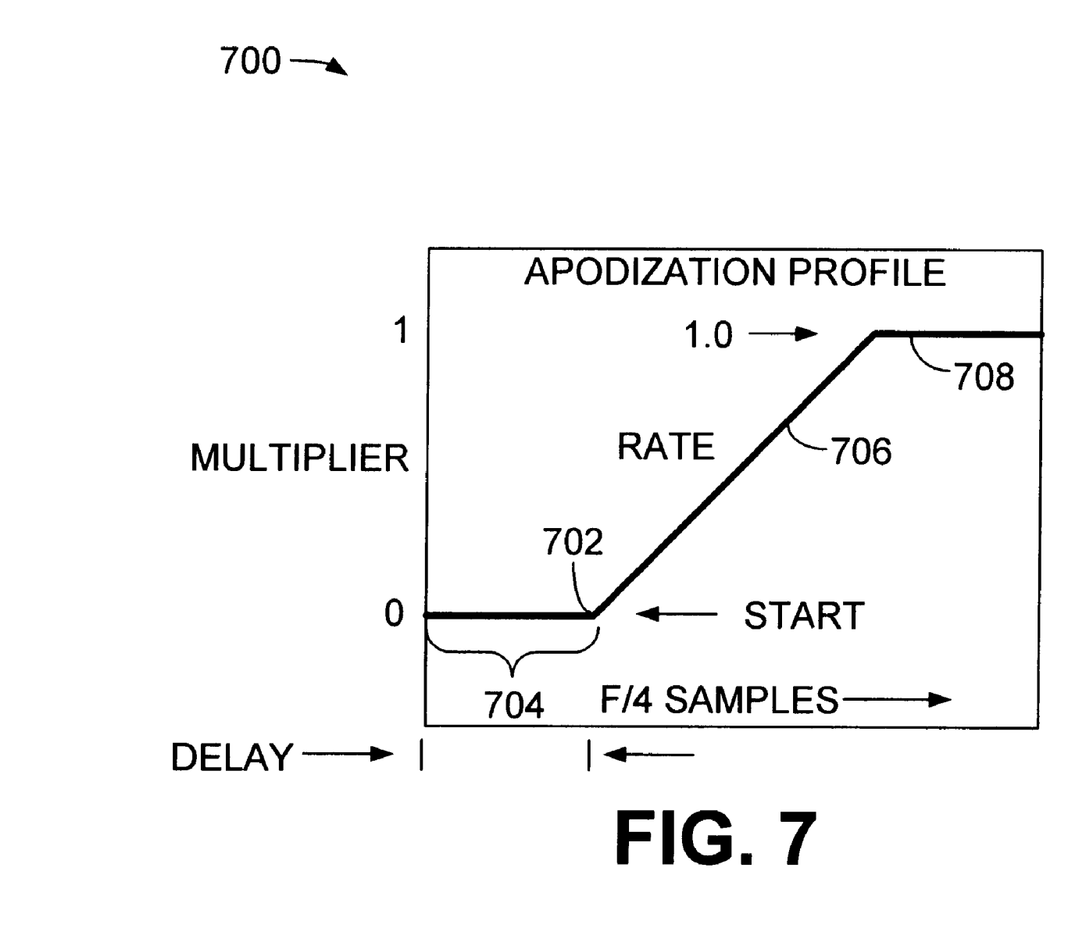
FIG. 7 is a graphical illustration showing the operation of the receive apodization element of FIG. 3.

FIG. 7 is a graphical illustration 700 showing the operation of the RX APOD element 314 of FIG. 3. The RX APOD element 314 multiplies the samples by a value between 0 and 1 that is set by the RX APOD control element 322 via connection 324 (FIG. 3). The apodization multiplier includes a profile of values that are defined by the start value, indicated using reference numeral 702, a delay value indicated using reference numeral 704 and a rate value indicated using reference numeral 706. The RX APOD element 314 uses the start value for the multiplier at the start of a line and applies this value to the multiplier for a number of samples defined by the delay value. Once the delay value times out, the multiplier is then incremented by the rate value for every sample until it reaches its full scale value of one indicated using reference numeral 708. The RX APOD element 314 counts samples at an "F/4" rate where "F" is the frequency. The delay time increments at this rate and the rate value is added to the apodization value at this sample rate. This low rate is used instead of the 4F sample rate because it reduces the size of the hardware needed to implement the RX APOD control element 322, while providing an adequate apodization update rate. The apodization multiplier is 5 bits wide and its value is always positive. This size allows greater than 26 db of difference in apodization between any two active channels in the receive aperture, with sufficient resolution to reduce "banding" in the image as the apodization multipliers increase through a line.

It will be apparent to those skilled in the art that many modifications and variations may be made to the preferred embodiments of the present invention, as set forth above, without departing substantially from the principles of the present invention. For example, the present invention can be used in any low element count transducer array. Furthermore, the transmit ASIC 260 could be located in the portable processor 102 instead of the probe 106. Further still, an analog sub-beamformer may be used with the one-dimensional transducer array to supply the delayed subarray signals to the main beamformer. Further still, the portability of the portable ultrasound system 100 can be enhanced through the selection and integration of various elements. All such modifications and variations are intended to be included herein within the scope of the present invention, as defined in the claims that follow.

What is claimed is:

1. An ultrasound imaging apparatus including a one-dimensional ultrasonic transducer array, comprising:
    a one-dimensional ultrasonic transducer array including a plurality of transducer elements divided into a plurality of subarrays; and
    receive circuitry coupled to the one-dimensional ultrasonic transducer array, the receive circuitry including a sub-beamformer configured to receive ultrasonic energy from the plurality of transducer elements and develop a plurality of delayed subarray signals corresponding to the plurality of subarrays.

2. The ultrasound imaging apparatus of claim 1, wherein the sub-beamformer further comprises:
    a coarse delay element;
    a fine delay element;
    a focus generator; and
    a summing apparatus.

3. The ultrasound imaging apparatus of claim 2, wherein the coarse delay element, fine delay element and focus generator are implemented digitally.

4. The ultrasound imaging apparatus of claim 3, wherein the coarse delay element further comprises:
    a synchronous dual-port random access memory; and
    a plurality of registers, wherein the ultrasonic energy received from the plurality of transducer elements is delayed by an integer number of clock cycles.

5. The ultrasound imaging apparatus of claim 3, wherein the fine delay element further comprises:
    a plurality of shift registers configured to receive the output of the coarse delay element;
    a plurality of barrel shifters configured to delay the ultrasonic energy received from the plurality of transducer elements by less than one clock cycle; and
    a summer configured to add the outputs of the plurality of barrel shifters.

6. The ultrasound imaging apparatus of claim 3, wherein the focus generator further comprises:
    logic configured to develop a control signal for the coarse delay element and the fine delay element.

7. The ultrasound imaging apparatus of claim 1, wherein the sub-beamformer is implemented on an application specific integrated circuit (ASIC).

8. The ultrasound imaging apparatus of claim 7, wherein the receive circuitry further comprises an analog-to-digital converter configured to sample the ultrasonic energy received from the plurality of transducer elements and configured to supply the sampled signals to the sub-beamformer, and wherein the analog-to-digital converter is implemented on the application specific integrated circuit (ASIC).

9. The ultrasound imaging apparatus of claim 1, wherein the receive circuitry further comprises:
    an analog-to-digital converter configured to sample the ultrasonic energy received from the plurality of transducer elements and configured to supply the sampled signals to the sub-beamformer, wherein the analog-to-digital converter and the sub-beamformer are implemented on an analog application specific integrated circuit (ASIC).

10. The ultrasound imaging apparatus of claim 1, further comprising a main beamformer configured to receive the plurality of delayed sub-array signals and develop a single beamformed signal.

11. The ultrasound imaging apparatus of claim 10, wherein the main beamformer further comprises:
    a coarse delay element;
    a fine delay element;
    a focus generator; and
    a summing apparatus.

12. The ultrasound imaging apparatus of claim 11, wherein the coarse delay element, fine delay element and focus generator are implemented digitally.

13. The ultrasound imaging apparatus of claim 11, wherein the main beamformer is implemented on an application specific integrated circuit (ASIC).

14. The ultrasound imaging apparatus of claim 1, further comprising transmit circuitry coupled to the plurality of transducer elements and configured to communicate transmit energy to the plurality of transducer elements.

15. The ultrasound imaging apparatus of claim 14, wherein the transmit circuitry is implemented on a transmit application specific integrated circuit (ASIC).

16. The ultrasound imaging apparatus of claim 15, wherein the sub-beamformer, the transmit ASIC and the ultrasonic transducer array are located in a transducer probe assembly.

17. The ultrasound imaging apparatus of claim 15, wherein the sub-beamformer, the transmit ASIC and the ultrasonic transducer array are located in a portable processor.

18. The ultrasound imaging apparatus of claim 15, wherein the transmit ASIC further comprises:
    an additional processor associated with the one-dimensional ultrasonic transducer array, the additional processor configured to amplify, filter and time gain compensate the ultrasonic energy received from the plurality of transducer elements.

19. An ultrasound imaging apparatus including a one-dimensional ultrasonic transducer array, comprising:
    a one-dimensional ultrasonic transducer array including a plurality of transducer elements divided into a plurality of subarrays;
    receive circuitry coupled to the one-dimensional ultrasonic transducer array, the receive circuitry including a sub-beamformer configured to receive ultrasonic energy from the plurality of transducer elements and develop a plurality of delayed subarray signals corresponding to the plurality of subarrays; and
    a main beamformer configured to receive the plurality of delayed sub-array signals and develop a single beamformed signal.

20. A method for sub-beamforming in a portable ultrasound imaging apparatus including a one-dimensional ultrasonic transducer array, the method comprising the steps of:
    dividing a one-dimensional ultrasonic transducer array including a plurality of transducer elements into a plurality of subarrays;

receiving, in receive circuitry coupled to the one-dimensional ultrasonic transducer array, ultrasonic energy from the plurality of transducer elements; and developing a plurality of delayed subarray signals corresponding to the plurality of subarrays.

21. The method of claim 20, wherein the developing step further includes the step of selectively delaying the ultrasonic energy from the plurality of transducer elements to generate the delayed subarray signals.

22. The method of claim 21, further comprising the steps of:

combining the plurality of delayed subarray signals; and developing a single beamformed signal.

23. A computer readable medium having a program for sub-beamforming in a portable ultrasound imaging apparatus including a one-dimensional ultrasonic transducer array, the program comprising:

a code segment for receiving, in receive circuitry coupled to the one-dimensional ultrasonic transducer array, ultrasonic energy from the plurality of transducer elements; and a code segment for developing a plurality of delayed subarray signals corresponding to the plurality of subarrays.

24. The program of claim 23, further comprising a code segment for selectively delaying the ultrasonic energy from the plurality of transducer elements to generate the delayed subarray signals.

25. The program of claim 24, further comprising:

a code segment for combining the plurality of delayed subarray signals; and a code segment for developing a single beamformed signal.

26. A portable ultrasound imaging apparatus including a one-dimensional ultrasonic transducer array, comprising:

an ultrasonic probe assembly containing a one-dimensional ultrasonic transducer array including a plurality of transducer elements divided into a plurality of subarrays; and a housing containing receive circuitry coupled to the one-dimensional ultrasonic transducer array, the receive circuitry including a sub-beamformer configured to receive ultrasonic energy from the plurality of transducer elements and develop a plurality of delayed subarray signals corresponding to the plurality of subarrays, wherein the housing and the ultrasonic probe assembly weigh less than fifteen (15) pounds.

27. The portable ultrasound imaging apparatus of claim 26, wherein the sub-beamformer further comprises:

a coarse delay element;

a fine delay element;

a focus generator; and a summing apparatus.

28. The portable ultrasound imaging apparatus of claim 27, wherein the coarse delay element, fine delay element and focus generator are implemented digitally.

29. The portable ultrasound imaging apparatus of claim 28, wherein the coarse delay element further comprises:

a synchronous dual-port random access memory; and a plurality of registers, wherein the ultrasonic energy received from the plurality of transducer elements is delayed by an integer number of clock cycles.

30. The portable ultrasound imaging apparatus of claim 28, wherein the fine delay element further comprises:

a plurality of shift registers configured to receive the output of the coarse delay element;

a plurality of barrel shifters configured to delay the ultrasonic energy received from the plurality of transducer elements by less than one clock cycle; and a summer configured to add the outputs of the plurality of barrel shifters.

31. The portable ultrasound imaging apparatus of claim 28, wherein the focus generator further comprises:

logic configured to develop a control signal for the coarse delay element and the fine delay element.

32. The portable ultrasound imaging apparatus of claim 26, wherein the housing and the ultrasonic probe assembly weigh less than six (6) pounds.

33. The portable ultrasound imaging apparatus of claim 26, wherein the sub-beamformer is implemented on an application specific integrated circuit (ASIC).

34. The portable ultrasound imaging apparatus of claim 33, wherein the receive circuitry further comprises an analog-to-digital converter configured to sample the ultrasonic energy received from the plurality of transducer elements and configured to supply the sampled signals to the sub-beamformer, and wherein the analog-to-digital converter is implemented on the application specific integrated circuit (ASIC).

35. The portable ultrasound imaging apparatus of claim 26, wherein the receive circuitry further comprises:

an analog-to-digital converter configured to sample the ultrasonic energy received from the plurality of transducer elements and configured to supply the sampled signals to the sub-beamformer, wherein the analog-to-digital converter and the sub-beamformer are implemented on an analog application specific integrated circuit (ASIC).

* * * * *